US00PP22173P3

(12) United States Plant Patent
Hart

(10) Patent No.: US PP22,173 P3
(45) Date of Patent: Oct. 4, 2011

(54) FEIJOA VARIETY NAMED 'KAKARIKI'

(50) Latin Name: *Acca sellowiana*
Varietal Denomination: Kakariki

(76) Inventor: Roy Hart, Mouteka (NZ)

( * ) Notice: Subject to any disclaimer, the term of this patent is extended or adjusted under 35 U.S.C. 154(b) by 148 days.

(21) Appl. No.: 12/378,017

(22) Filed: Feb. 10, 2009

(65) Prior Publication Data

US 2009/0151032 P1 Jun. 11, 2009

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP8,825 P 7/1994 Patterson et al.
PP21,614 P3 1/2011 Hart

OTHER PUBLICATIONS

Anonymous. "Waimea Feijoas". Available at: http://www.waimeanurseries.co.nz/bin/nfdetail.php?code_no=PFG_FSubVarietyDev accessed Jun. 15, 2010.*
Anonymouse. "Feijoa Varieties" Available at: http://www.feijoa.org.nz/varieties.html accessed Jun. 15, 2010.*
U.S. Appl. No. 12/322,988, for Feijoa Varity Named 'Kaiteri', filed Feb. 10, 2009.

* cited by examiner

*Primary Examiner* — Wendy C Haas
(74) *Attorney, Agent, or Firm* — Paine Hamblen, LLP

(57) ABSTRACT

A new and distinct variety of feijoa plant denominated as 'kakariki' is described and which is characterized as to novelty by producing a fruit which is ripe for harvesting under the ecological conditions prevailing near Nelson, New Zealand at least as early 28 March.

3 Drawing Sheets

Latin name: '*Acca sellowiana*'.
Varietal designation: 'Kakariki'.

BACKGROUND OF THE NEW VARIETY

The present invention relates to a new and distinct variety of feijoa '*Acca sellowiana*' and more specifically to a feijoa variety which produces fruit which are ripe for harvesting in the very early season, that is, from at least as early as about 28 Mar. 2008 under the ecological conditions prevailing near Nelson, New Zealand.

It has long been recognized that it would be desirable to provide a feijoa variety that bears a crop earlier in the season then those varieties that it is most closely similar to, and under the ecological conditions prevailing near Nelson, New Zealand. In this regard, several well known and popular feijoa varieties are harvested in both the early and late seasons near Nelson, New Zealand. However, their respective fruit sizes are relatively small, on average, when compared to the large fruit size produced by the present variety of feijoa. More specifically, the variety of feijoa identified by the varietal name 'Opal Star' (U.S. Plant Pat. No. 8,825) is characterized by producing a relatively small sized fruit (about 85 grams) during the late season, that is, from about 16 May 2008 under the ecological conditions prevailing near Nelson, New Zealand. Still further, the variety 'Apollo' (unpatented), produces an average sized fruit weighing about 100 grams and which is ripe for harvesting about 18 Apr. 2008 under the same ecological conditions. Still further, the unpatented variety 'Triumph' produces a small fruit (about 85 grams) and which is ripe for harvesting about 23 May 2008 under the same ecological conditions. Yet further, the variety 'Unique' (unpatented) also produces a small fruit (about 85 grams), and which is ripe in the early season for harvesting, that is, on or about 18 Apr. 2008 under the ecological conditions prevailing near Nelson, New Zealand. Moreover, the present variety is similar in some respects to the feijoa variety 'Kaiteri' (U.S. Plant patent pending, Ser. No. 12/322,988), and which is ripe for harvesting in the very early season, that is, on or after about 4 Apr. 2008, under the ecological conditions prevailing near Nelson, New Zealand. Still further, the new variety is somewhat similar to the variety named 'Anatoki' (U.S. Plant patent pending, Ser. No. 12/378,015), and which produces a relatively large sized fruit (about 100 grams) in the very early season, that being on or after 11 Apr. 2008 under the current ecological conditions prevailing near Nelson, New Zealand. In contrast, the present variety of feijoa is distinguished therefrom and characterized as to novelty by producing a large fruit (greater than about 125 grams) in the very early season, that being as early as 28 Mar. 2008 under the ecological conditions prevailing near Nelson, New Zealand. In view of its early harvesting date, and large size, the present variety provides a degree of commercial and consumer appeal not present with respect to other known varieties.

ORIGIN ASEXUAL REPRODUCTION

The present variety of feijoa was derived from a selective cross-pollination of the unpatented feijoa variety 'Apollo' and an unnamed seedling which was conducted in the cultivated area of the Applicant's farm during the 1996 growing season. The present variety 'Kakariki' was first asexually reproduced from cuttings taken from this first asexually reproduced plant. Subsequent thereto, it has been established that the asexually reproduced plants derived from these cuttings are true over several successive generations. The present variety is unique and novel as to other varieties it is most closely similar to by producing a large sized fruit having an average weight of at least about 125 grams and which is ripe for harvesting on or after 28 Mar. 2008 under the ecological conditions prevailing near Nelson, New Zealand.

BRIEF DESCRIPTION OF THE DRAWINGS

The accompanying drawings which are provided are color photographs of the new variety of feijoa. The colors in these photographs are as nearly true as is reasonably possible on a color representation of this type. Due to chemical development, processing, and printing, the leaves and fruit depicted in these photographs may or may not be accurate when compared to the actual specimen. For this reason, future color references should be made to the color plates as provided by The Royal Horticulture Society Colour Charts (1995 Edition).

NOT A COMMERCIAL WARRANTY

Figure 1:
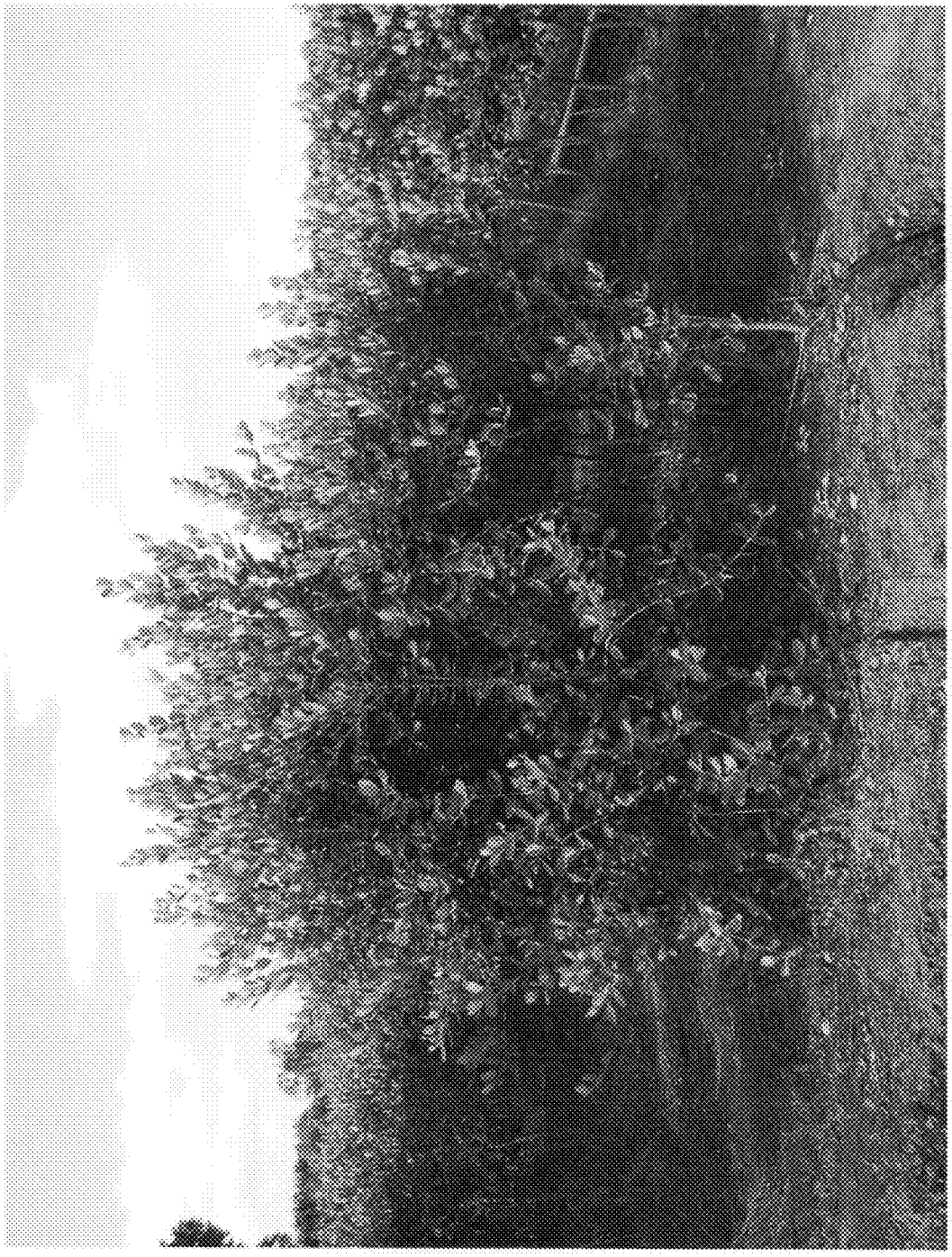
FIG. 1 is a color photograph of the new feijoa variety growing on its own roots and which is approximately 4 years old.
Figure 2:
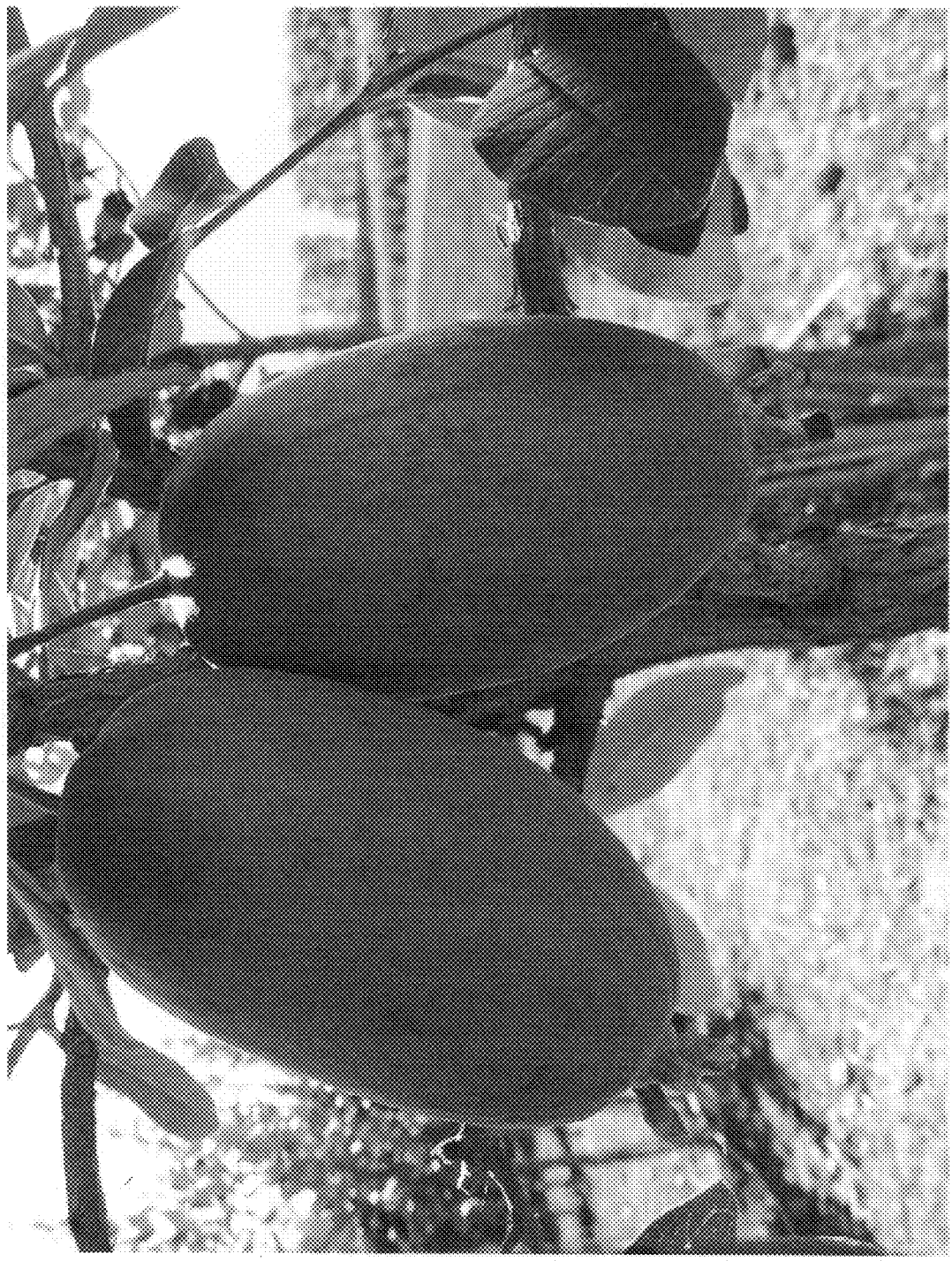
FIG. 2 is a photograph of typical fruit which are sufficiently matured for harvesting.
Figure 3:
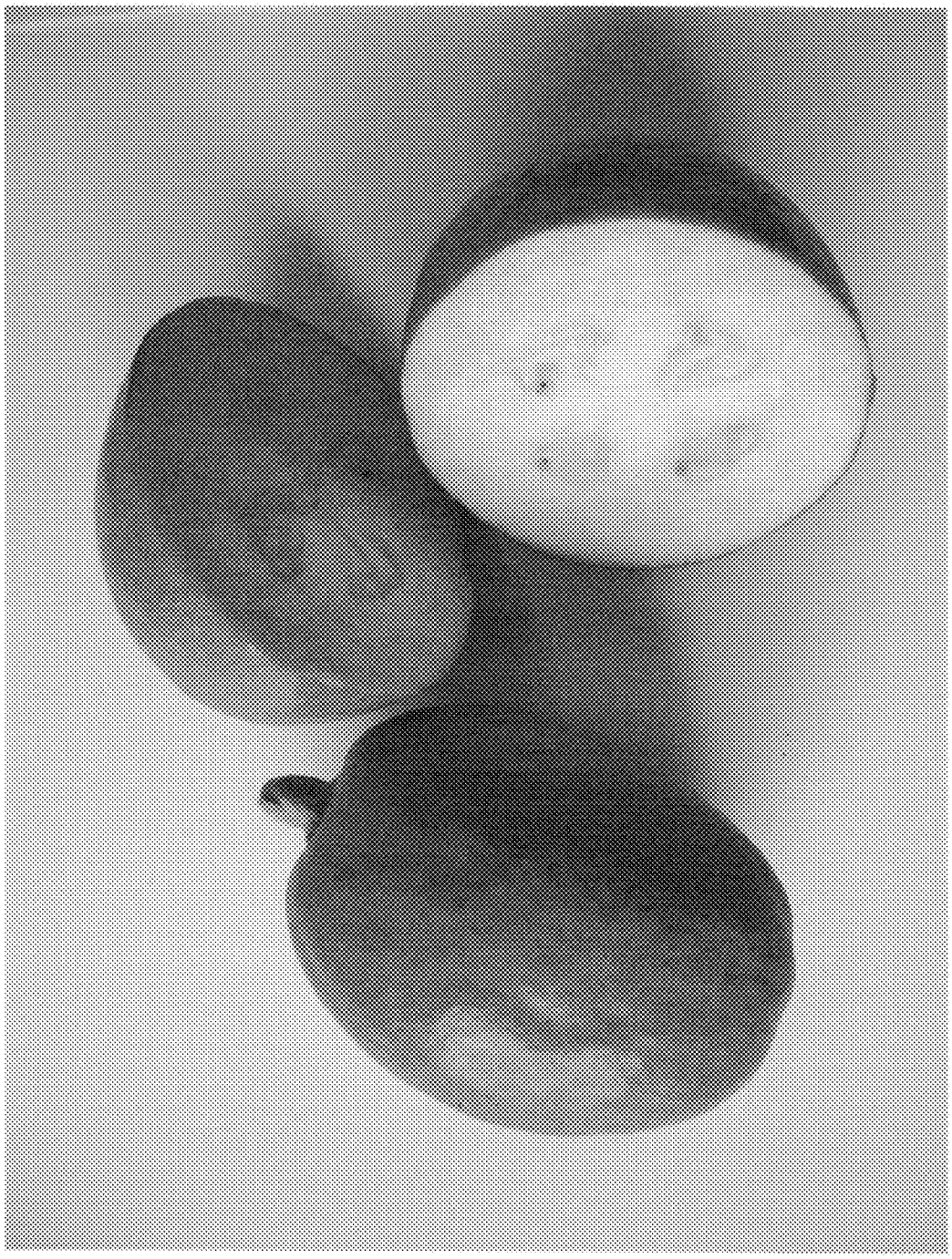
FIG. 3 is a picture of two fruit of the present variety, one of which is divided in the equatorial plane to show the flesh characteristics thereof.

The following detailed description has been prepared to solely comply with the provisions of 35 USC §112, and does not constitute a commercial warranty (either expressed or implied), that the present variety will, in the future, display the botanical, pomological or other characteristics as set forth hereinafter. Therefore, this disclosure may not be relied upon to support any future legal claims, which include, but are not limited to breach of warranty of merchantability, fitness for any particular purpose, or non-infringement which is directed in whole, or in part, to the present variety.

DETAILED DESCRIPTION

Tree:

*Size.*—Height — About 2 meters.

*Crown diameter.*—About 2 meters when measured at a distance of about 1 meter above the ground.

*Vigor.*—Average for the species.

*Tree form.*—Ramified.

*Growth habit.*—Considered spreading.

Trunk:

*Diameter.*—About 7 cm. when measured at a distance of about 20 cm. above the ground.

*Bark texture.*—Rough, and somewhat flaky.

*Bark color.*—Grey-brown (RHS 199B).

Leaves:

*Leaf length.*—On average about 70 mm.

*Leaf width.*—On average about 35 mm.

*Leaf shape.*—Elliptical.

*Marginal form.*—Generally — Straight.

*Leaf color.*—Upper surface — Green (RHS 139A).

*Leaf color.*—Lower surface — Grey-green (RHS 190C).

Flowers:

*Quantity of flowers per cluster.*—4 or 5 flowers may be found per cluster.

*Flower petals.*—Quantity — 4.

*Flower petal color.*—Upper surface — White (RHS 155C).

*Flower petal color.*—Lower surface — Red-purple (RHS 65D).

*Sepals.*—Numbers — 4.

*Stamins.*—Numbers — Numerous.

*Stamins.*—Color — Red (RHS 45C).

*Pistil.*—Numbers — 1.

*Pistil.*—Color — Red (RHS 45A).

*Pollination.*—Generally — Self-infertile. The inventor has discovered that any other feijoa variety that flowers at approximately the same time of the season may be a suitable pollinator.

Fruit:

Fruit size: At full commercial maturity, the fruit is considered to be large and has an average fruit weight of about 100 grams.

*Fruit length.*—About 80 mm.

*Fruit width.*—About 55 mm.

*Fruit shape.*—Considered elongated and obovoid when considered in profile.

*Fruit skin texture.*—Irregularly bumpy.

*Fruit skin color.*—Green (RHS 143C).

*Fruit flesh.*—Texture — Smooth and soft.

*Fruit flesh flavor.*—Sweet with some acid. The fruit flesh is considered aromatic.

*Brix.*—At the appropriate harvesting time, about 12 degrees.

*Flesh.*—Color — White (RHS 157C).

*Ripe for harvesting and shipment.*—Considered very early from at least about 28 Mar. 2008 under the ecological conditions prevailing near Nelson, New Zealand.

*Fruit use.*—For local fresh markets and processed consumption.

*Fruit storage.*—About 16 days at a temperature of 1 degree Celsius. The fruit of the present variety has a shelf life of about 2 to 7 days.

Although the new variety of feijoa herein denominated as 'Kakariki' possesses the described characteristics when grown under the ecological conditions prevailing near Nelson, New Zealand, it should be understood that variations of the usual magnitude and characteristics incident to changes in growing conditions, fertilization, pruning and pest control are to be expected.

Having thus described and illustrated my new variety of feijoa, what I claim is new, and desire to secure by Plant Letters Patent is:

1. A new and distinct variety of feijoa plant substantially as illustrated and described and which is characterized as to novelty by producing a large fruit which is mature for harvesting under the ecological conditions prevailing near Nelson, New Zealand at least as early as about 28 March.

* * * * *